United States Patent [19]

Diamantopoulos

[11] Patent Number: 5,409,482
[45] Date of Patent: Apr. 25, 1995

[54] PROBE, AND METHOD OF USE THEREOF FOR BIOMODULATION OF TISSUE, NERVE AND IMMUNE SYSTEMS

[75] Inventor: Costas Diamantopoulos, London, United Kingdom

[73] Assignee: Omega Universal Holdings Limited, London, United Kingdom

[21] Appl. No.: 768,725

[22] PCT Filed: Feb. 8, 1991

[86] PCT No.: PCT/GB91/00197
§ 371 Date: Oct. 11, 1991
§ 102(e) Date: Oct. 11, 1991

[87] PCT Pub. No.: WO91/12050
PCT Pub. Date: Aug. 22, 1991

[30] Foreign Application Priority Data

Feb. 9, 1990 [GB] United Kingdom .................. 9002957

[51] Int. Cl.⁶ .............................................. A61B 6/00
[52] U.S. Cl. .......................................... 606/13; 606/3; 606/10; 607/89; 607/90
[58] Field of Search .................. 128/395, 397, 398; 606/2–19; 607/89, 90

[56] References Cited

U.S. PATENT DOCUMENTS

| | | | |
|---|---|---|---|
| 4,232,678 | 11/1980 | Skovajsa | 128/395 |
| 4,297,653 | 10/1980 | Scifres et al. | 331/94.5 |
| 4,380,074 | 4/1983 | Walsh | 372/43 |
| 4,391,275 | 7/1983 | Fankhauser et al. | 606/4 |
| 4,538,276 | 8/1983 | Sequeira et al. | 372/6 |
| 4,601,288 | 7/1986 | Myers | 606/6 |
| 4,803,689 | 2/1989 | Shibanuma | 372/36 |
| 4,826,431 | 5/1989 | Fujimura et al. | 606/15 |
| 4,834,491 | 5/1989 | Aoki et al. | 434/63 |

FOREIGN PATENT DOCUMENTS

| | | | |
|---|---|---|---|
| 0065223 | 11/1982 | European Pat. Off. | |
| 0320080 | 6/1989 | European Pat. Off. | 128/395 |

*Primary Examiner*—David M. Shay
*Attorney, Agent, or Firm*—Shoemaker and Mattare, Ltd.

[57] ABSTRACT

The probe for biomodulation is disclosed. The probe includes a semiconductor laser and a drive circuit which causes the laser to generate pulses in bursts. The pulses themselves are of nanosecond or picosecond duration, while the bursts are of millisecond, microsecond, or nanosecond duration. The pulses can be delivered at rates up to 3 GHz. The probe also includes a heat sink as the body contacting portion.

6 Claims, 2 Drawing Sheets

PROBE, AND METHOD OF USE THEREOF FOR BIOMODULATION OF TISSUE, NERVE AND IMMUNE SYSTEMS

This invention relates to probes, and methods of use thereof, for biomodulation of tissue, nerve and immune systems by frequency modulation of semiconductor lasers.

It has become apparent, through our recent research, that an important parameter for the observed laser biomodulation effect (stimulation or inhibition) is the method of delivering the visible or invisible light energy into the target material. We have also demonstrated that all other conditions being constant (e.g. wavelength, power density and energy density) the pulsing frequency and pulsing duration modulation of the laser light varies the biomodulation action.

It is, therefore, one object of the present invention, to provide a probe wherein the pulsing frequency and pulsing duration modulation can be very economically and efficiently controlled and applied.

According to the invention, there is provided a probe for the biomodulation of tissue, nerve and immune systems having a semiconductor laser mounted thereon for delivering an electromagnetic beam to the area to be treated and electronic means so mounted within the probe closely adjacent the laser for stimulating the laser for controlling the generation of pulses and the emission of a pulsating visible or invisible infrared light constituting the said beam as thereby substantially to eliminate losses due to radio frequency and microwave generation. Very advantageously the electronic means is arranged to pulse the laser light with micropulses of nanosecond or picosecond duration and then modulate the light again by pulsing the laser with macropulses of millisecond, microsecond or nanosecond duration.

The invention also includes the method of effecting biomodulation (stimulation or inhibition) by delivering visible or invisible light energy into a target tissue, nerve or immune system by means of a probe as aforesaid.

In order that the invention may be clearly understood and readily carried into effect a probe and manner of operating such probe for biomodulation of tissue, nerve or an immune system will now be described, by way of example, with reference to the accompanying drawings, in which.

Figure 1:
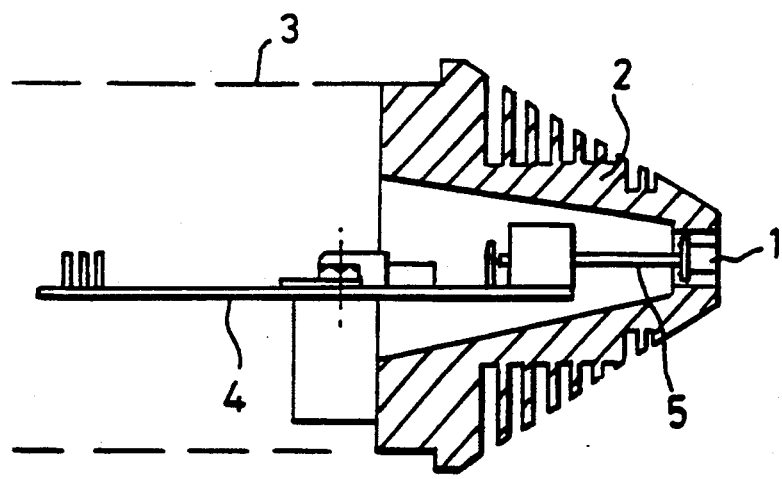
FIG. 1 is a diagrammatic sectional elevation of the probe.
Figure 2:
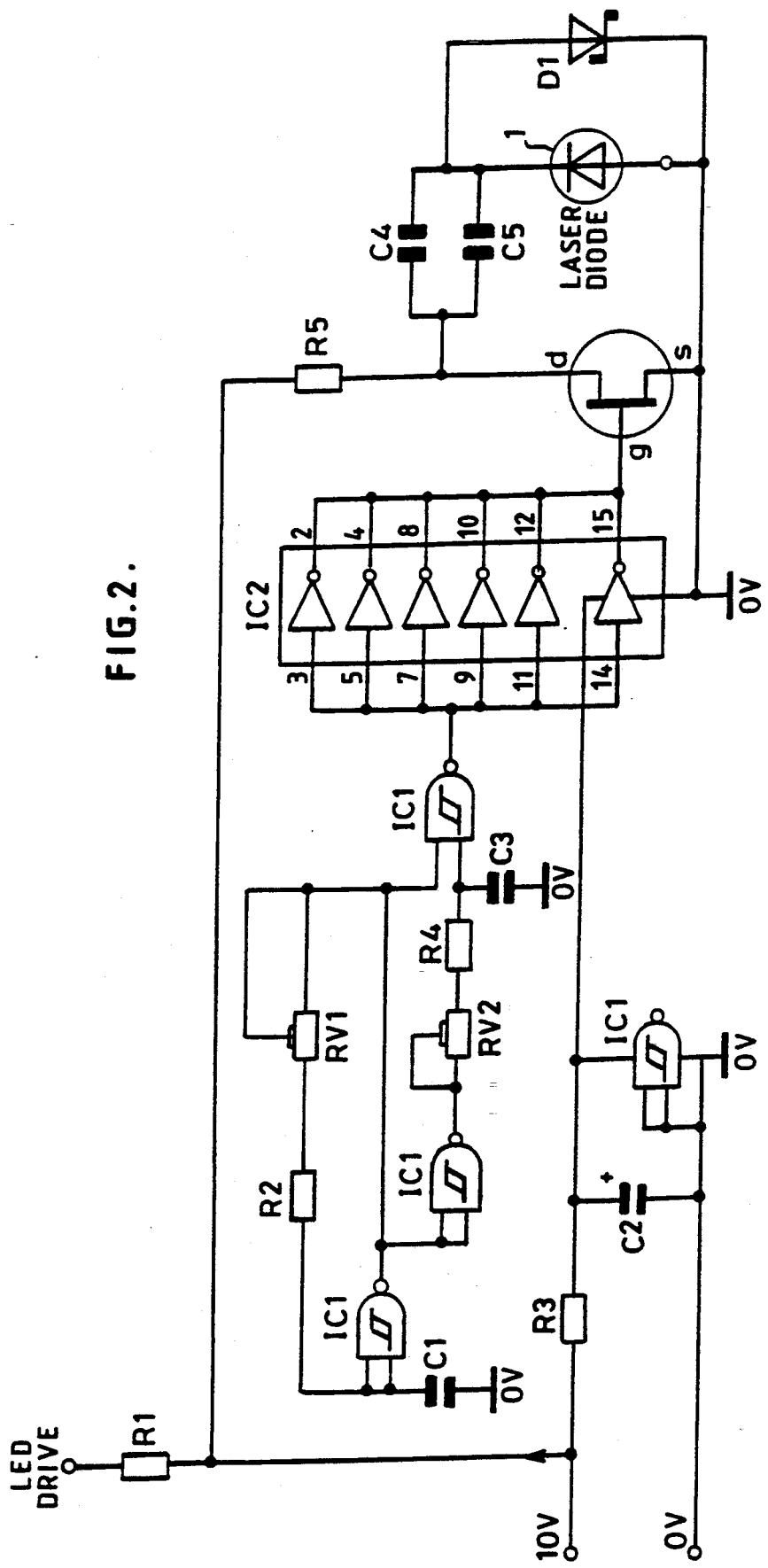
FIG. 2 is a circuit diagram comprising an electrical assembly in the probe.

Referring to FIG. 1, the probe comprises a laser diode 1 for projecting a monochromatic beam in the visible or infrared range of the spectrum from the tip of a tapered and finned heat sink 2 terminating the probe 3. The laser diode 1 is driven and controlled through the medium of an electronic laser drive circuit means (FIG. 2) carried by a printed circuit board 4 and connected to the laser diode 1 by a sleeved lead 5. As shown, the semiconductor laser 1 is mounted at and within the apex portion of a conical heat sink (2) included in and terminating the probe.

Figure 3:
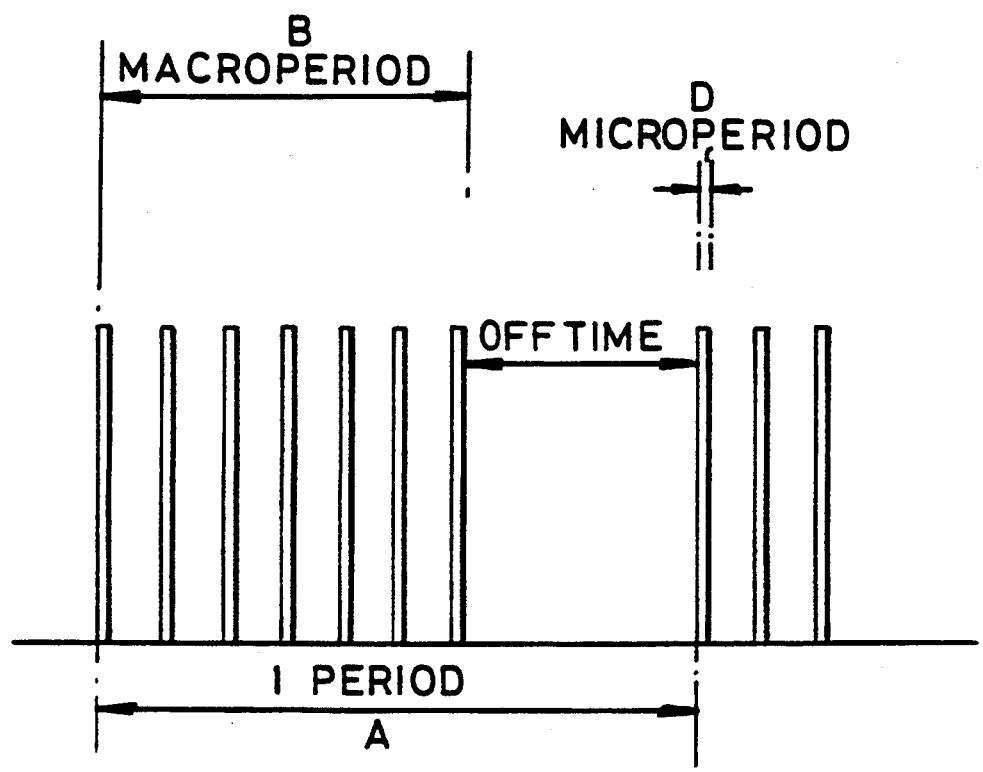
FIG. 3 is an explanatory diagram.

The circuit comprises oscillator frequency control, beam oscillator, beam power control, beam power supply and beam control logic as described in Patent Application No. EP-A-0320080 and the circuit is arranged for the beam to be modulated periodically to operate as shown in FIG. 3. Thus, in each duty period A there is a macroperiod B followed by an off time C. In each macroperiod B there is a series of similar microperiods D. The following table shows experimental results obtained with this form of operation with an output wavelength of 850 mm and a series of oscillator frequencies ranging from 2.5 Hz and 5 KHz.

| 850 3 ML FREQUENCY | PROBE DUTY PERIOD A | PULSE CYCLE OFF-TIME C | WIDTHS 80% MACRO-PULSE B | MICRO-PULSE D | No. of MICRO PER MACRO |
|---|---|---|---|---|---|
| 2.4 Hz | 400 msec | 80 mSec | 320 mSec | 350 nSec | 96.969 |
| 5 Hz | 200 mSec | 40 mSec | 160 mSec | 350 nSec | 48,484 |
| 10 Hz | 100 mSec | 20 mSec | 80 mSec | 350 nSec | 24,242 |
| 16 Hz | 62.5 mSec | 12.5 mSec | 50 mSec | 350 nSec | 15,151 |
| 20 Hz | 50 mSec | 10 mSec | 40 mSec | 350 nSec | 12,121 |
| 40 Hz | 25 mSec | 5 mSec | 20 mSec | 350 nSec | 6,060 |
| 80 Hz | 12.5 mSec | 2.5 mSec | 10 mSec | 350 nSec | 3,030 |
| 160 Hz | 6.25 mSec | 1.25 mSec | 5 mSec | 350 nSec | 1,515 |
| 292 Hz | 3.42 mSec | 684 Sec | 2.74 mSec | 350 nSec | 830 |
| 700 Hz | 1.43 mSec | 286 uSec | 1.14 mSec | 0350 nSec | 345 |
| 1 KHz | 1 mSec | 200 uSec | 800 uSec | 350 nSec | 242 |
| 5 KHz | 200 Sec | 40 uSec | 160 uSec | 350 nSec | 48 |

By way of example, in one application of a system as described above the electromagnetic output laser beam has a wavelength of 850 mm and a frequency of $352.9 \times 10^3$ GHz pulsed at 300,000 and additionally modulated at a frequency of from 1 Hz to 2 GHz. Above a pulsation frequency of 5000 Hz radio frequencies also arise and in order to avoid the losses due to transverse dispersion that these would involve if transmitted along a cable the printed circuit board 4 is located in the probe itself as shown in FIG. 1.

In summary the invention enables the semiconductor laser light to be pulsed up to 3 GHz with micropulses of nanosecond or picosecond duration and when modulated again with a carrier frequency by pulsing the diode with macropulses of millisecond, microsecond or nanosecond duration. The macropulses can be square or sinusoidal in shape whilst the micropulses are square. By incorporating the circuitry in the head of the probe interference from radio frequency (KHz, uHz) and microwave (GHz) generation is eliminated.

I claim:

1. A probe (3) for biomodulation of tissue, nerve and immune systems comprising a semiconductor laser (1) mounted within said probe for delivering an electromagnetic beam to said tissue, nerve and immune systems to be treated, and electronic laser drive circuit means (4, 5) mounted closely adjacent said laser (1) and within said probe (3), for controlling the generation of pulses and stimulating the said laser (1) for emitting pulsating visible or invisible infrared light constituting the said electromagnetic beam to thereby substantially eliminate losses due to radio frequency and microwave generation.

2. A probe according to claim 1, characterised in that said electronic laser drive circuit means (4, 5) pulses the electromagnetic beam of said laser (1) with micropulses of nanosecond or picosecond duration and then modulates said beam again by pulsing the laser (1) with macropulses of millisecond, microsecond or nanosecond duration.

3. A probe according to claim 2, wherein said laser light of said laser (1) is pulsed up to 3 GHz.

4. A probe according to claim 2 or claim 3, wherein said macropulses are square or sinusoidal in shape and said micropulses are square in shape.

5. A method of effecting biomodulation of tissue, nerve and immune systems, including the steps of:
a) delivering visible or invisible light energy into a target tissue, nerve and immune system via a probe having mounted thereon a semiconductor laser for delivering an electromagnetic beam to said tissue, nerve and immune systems to be treated, and electronic laser drive circuit means so mounted within said probe and closely adjacent to said laser, for controlling the generation of pulses and stimulating the said laser for emitting visible or invisible light energy into said target tissue, nerve and immune systems, as thereby substantially to eliminate losses due to radio frequency and microwave generation.

6. A probe (3) according to claim 1, wherein said probe includes a conical heat sink (2) having an apex portion terminating the said probe, said semiconductor laser (1) being mounted within said apex portion.

* * * * *